United States Patent [19]

Sweeny et al.

[11] Patent Number: 5,225,591

[45] Date of Patent: Jul. 6, 1993

[54] PROCESS FOR MAKING 1-CYCLOPENTYLALYL AMINES USEFUL FOR THE SYNTHESIS OF SWEETENERS

[75] Inventors: James G. Sweeny, Atlanta; Lihong L. D'Angelo, Decatur, both of Ga.

[73] Assignee: The Coca-Cola Company, Atlanta, Ga.

[21] Appl. No.: 922,705

[22] Filed: Jul. 28, 1992

[51] Int. Cl.$^5$ ............................................. C07C 61/06
[52] U.S. Cl. ................................. 562/503; 564/303; 564/455
[58] Field of Search ................ 564/455, 303; 562/503

[56] References Cited

U.S. PATENT DOCUMENTS 4,411,925 10/1983 Brennan ............................ 426/548
4,946,993 8/1990 Cortes et al. .

OTHER PUBLICATIONS

"Compendium of Organic Synthesis Methods," Wiley-Interscience, N.Y., vol. I (1971, ed., I. T. Harrison and S. Harrison), vol. II (1974, ed., I. T. Harrison and S. Harrison, vol. III (1977, ed., L. S. Hegedus and L. G. Wade), vol. IV (1980, ed. L. G. Wade), vol. V (1984, ed. L. G. Wade), Chapter 7.
L. Bonsignore et al, CA, 89, 108266 (1978), *Rend. Semin. Fac. Sci. Univ. Cagliari*, (1977), 47, 1–8.
P. A. Grieco, D. T. Parker, W. F. Fobare and R. Ruckle, *J. Amer. Chem. Soc.*, 109, 5859–5861 (1987).
Smith et al., J. Amer. Chem. Soc. 76, 4564–4567, (1954).
Bourgeois-Cury et al., *Tetrahedron Letters*, 33, 1277–1280 (1992).
S. D. Larsen and P. A. Grieco, *J. Amer. Chem. Soc.*, 107, 1768–1769 (1985).
P. A. Grieco and J. D. Clark, *J. Org. Chem.*, 55, 2271–2272 (1990).
P. A. Grieco and A. Bahsas, *J. Org. Chem.*, 52, 5746–5749 (1987).
M. Anwer et al., *Tet. Lett.*, 22 4369 (1981).
M. Anwer et al., *J. Org. Chem.*, 48, 3503 (1983).
S. Ram et al., *Tet. Lett.*, 25, 3415 (1984).
S. Ram et al., *Synthesis*, 133 (1986).
A. Barrett et al., *Tet. Lett.*, 29, 5733 (1988).
G. Brown et al., *Synthesis*, 1036 (1982).
J. Weir et al., *J. Org. Chem.*, 45, 4926 (1980).
Bundel et al., *J. Org. Chem.*, USSR (Engl. Transl.), 8, 751 (1972).

Primary Examiner—Michael L. Shippen

[57] ABSTRACT

The disclosed process relates to a method for preparing 1-cyclopentylalkyl amines, useful in the synthesis of artificial sweeteners, by reducing an azanorbornene in a high-yield one-step reduction of an azanorbornene, wherein the method involves use of a solvent reductant system with catalyst that is compatible with the production of edible food compositions.

29 Claims, No Drawings

PROCESS FOR MAKING 1-CYCLOPENTYLALYL AMINES USEFUL FOR THE SYNTHESIS OF SWEETENERS

FIELD OF THE INVENTION

This invention relates to a process for making 1-cyclopentylalkyl amines, which are useful for the synthesis of artificial sweeteners.

BACKGROUND OF THE INVENTION

L-aspartyl-D-alanine amides, such as disclosed in U.S. Pat. No. 4,411,925, are known to be useful as artificial sweeteners. Such amides may be synthesized by reacting a dipeptide precursor with an amine. The dipeptide precursors may be obtained using well known methods for the coupling of amino acids.

The amines required for producing the dipeptide amide sweeteners may typically be obtained via the reduction of a corresponding ketoxime using sodium-/alcohol mixtures. The ketoxime may be obtained from its corresponding ketone and the ketone in turn may be prepared by reaction of the corresponding acid chloride with a Grignard reagent in ether or tetrahydrofuran at low temperature. The overall process for preparing the amine required for use in the synthesis of dipeptide amide sweeteners, therefore, may involve the use of several reaction steps, costly starting materials and the difficulty of operating with highly flammable reagents under dry, oxygen-free atmospheres. Furthermore, the low yields of some of these reaction steps may lead to low overall yields for the combined reaction steps.

In general, known processes for preparing 1-cyclopentylalkyl amines involve preparation of an alkyl cyclopentane of type (II) and then converting it to the corresponding amine.

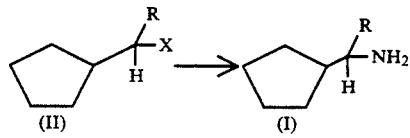

$X = COCl$, $CONH_2$, $CO_2H$, $OH$, $Br$, $NO_2$, $N_3$, $=O$, $=NOH$, $=NOCH_3$ (See "Compendium of Organic Synthesis Methods," Wiley-Interscience, N.Y., Vol. I (1971, ed., I. T. Harrison and S. Harrison), Vol. II (1974, ed., I. T. Harrison and S. Harrison, Vol. III (1977, ed., L. S. Hegedus and L. G. Wade), Vol. IV (1980, ed. L. G. Wade), Vol. V (1984, ed. L. G. Wade).

An example of the preparation of 1-cyclopentylethyl amine is reported in L. Bonsignore et al., CA, 89, 108266 (1978), Rend. Semin. Fac. Sci. Univ. Cagliari, (1977), 47, 1-8, wherein ethylidenecycloalkanes are hydroborated, hydrolyzed and oxidized to form the respective acetylcycloalkanes which are in turn aminated to give 1-cyclopentylethyl amine. Alternatively, cyclopentylalkyl amines may be obtained by reducing cyclopentyl methyl ketone in the presence of ammonium formate and formic acid, Smith et al., J. Amer. Chem. Soc. 76, 4564-4567, (1954).

The palladium-catalyzed reduction of bicyclic allylic ester amines to produce a cyclopentenyl glycine is described in Bourgeois-Cury et al., Tetrahedron Letters, 33, 1277-80 (1992).

Each of the above-mentioned procedures suffer from the use of multiple steps, costly starting materials, difficult reaction conditions, or low yields.

OBJECTS AND SUMMARY OF THE INVENTION

An object of the present invention is to provide an improved process for synthesizing dipeptide amide type artificial sweeteners that involves a reduced number of reaction steps using economic and readily available starting materials and economic, safe and convenient reaction conditions.

Another object of the present invention is to provide a process that may be safely used to prepare dipeptide amide compounds that are to be included in edible food compositions.

Another object of the present invention is to produce artificial sweeteners having a high sweetness potency.

A feature of the present invention is that the artificial sweeteners may comprise L-aspartyl-D-alanine-N-(S)-1-cyclopentylalkyl amides, wherein the amides are obtained from an S-enantiomer-enriched mixture of 1-cyclopentylalkyl amine.

A further feature of the present invention is that substituted azanorbornenes, such as a N-benzyl-3-alkyl-2-azanorborn-5-ene having the following structure:

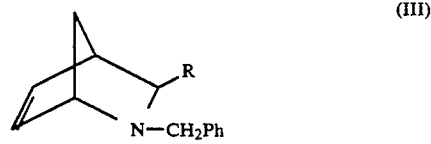

may be used to produce the 1-cyclopentylalkyl amines that are useful for the synthesis of artificial sweeteners.

Another feature of the present invention is that the azanorbornenes may be converted to the desired 1-cyclopentylalkyl amines in a high yield reaction in which reduction of the ring double bond of the azanorbornene occurs at room temperature in the same reaction step with cleavage of the ring C-N bond to form a ring-opened saturated amine that is easily purified.

Yet another feature of the present invention is that the one-step conversion of the azanorbornene to a 1-cyclopentylalkyl amine takes place in a lower alkyl alcohol solvent in the presence of acetic acid, ammonium formate and a palladium on charcoal catalyst.

An advantage of the present invention is that the azanorbornenes used to produce the 1-cyclopentylalkyl amines are relatively stable under basic conditions and can be stored for several months.

These, and still other objects, features and advantages, may be achieved using a process for making a 1-cyclopentylalkyl amine comprising the steps of reducing an N-benzyl-3-alkyl-2-azanorborn-5-ene in a lower alkyl alcohol solvent in the presence of acetic acid, ammonium formate and a transition metal catalyst to produce a 1-cyclopentylalkyl amine having the structure:

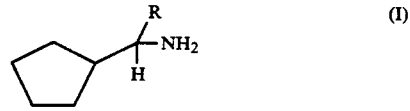

wherein R is an alkyl group. The R group may be a straight chain alkyl group of 1 to 4 carbons, a branched alkyl group of 3 to 6 carbons or a cycloalkyl group of 3 to 6 carbons.

The present invention also provides a process for making an artificial dipeptide amide sweetener comprising the steps of: preparing an (R,S) mixture of 1-cyclopentylalkyl amine by reducing an azanorbornene in a lower alkyl alcohol solvent in the presence of acetic acid, ammonium formate and a transition metal catalyst; enriching the (R,S) mixture to produce a mixture enriched with the S-enantiomer; coupling a protected L-aspartyl-d-α-amino alkanoic acid with the 1-cyclopentylalkyl amine of the enriched mixture to produce a protected-dipeptide-1-cyclopentylalkyl amide; and deprotecting the protected-dipeptide- 1-cyclopentylalkyl amide to produce an artificial dipeptide amide sweetener.

In particular, the present invention provides a process for making a 1-cyclopentylalkyl amine comprising: dissolving a N-benzyl-3-alkyl-2-azanorborn-5-ene compound in a lower alkyl alcohol solvent; adding a reducing composition of acetic acid, ammonium formate and a transition metal catalyst; reducing the N-benzyl-3-alkyl-2-azanorborn-5-ene with the reducing composition under an inert atmosphere; acidifying with an aqueous acid; removing the lower alkyl alcohol solvent by distillation; neutralizing the acid with an aqueous alkaline metal hydroxide up to a pH of about 8 to about 12; extracting the 1-cyclopentylalkyl amine with a suitable water-immersible organic solvent; and recovering the amine from the extract.

DETAILED DESCRIPTION OF THE INVENTION

The methods by which the foregoing objects, features and advantages of the present invention are achieved will now be described in more detail. These details provide a description of the invention for the purpose of enabling those skilled in the art to practice the invention, but without limiting the invention to the specific embodiments described.

The present invention is directed to a one-step reduction reaction of an azanorbornene:

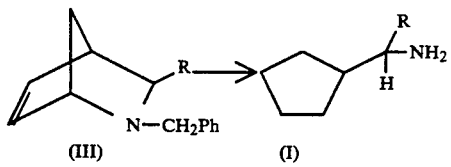

wherein R is an alkyl group. The alkyl group may be a straight chain alkyl group of, for example, 1 to 4 carbon atoms and/or a branched alkyl or cycloalkyl group of, for example, 3 to 6 carbon atoms. The reaction shown involves the reduction of the azanorbornene to a saturated amine in a single reaction-step transfer hydrogenolysis process and may be generally described as the direct cleavage of a bicyclic allylic amine compound to form a saturated 1-cycloalkyl-alkyl amine. In the method of the present invention, this reduction reaction is carried out in a suitable solvent/reduction system such as a mixture of a lower alkyl alcohol, acetic acid, ammonium formate and a transition metal catalyst. The method is characterized in that high yields are produced using reducing agents, solvents, catalysts and reaction conditions that are compatible with the preparation of compounds that may be safely used in the production of edible food compositions.

The azanorbornene used in the present invention to produce the 1-cyclopentylalkyl amine may, for example, be obtained in a process whereby an aldehyde, benzylamine hydrochloride and cyclopentadiene are reacted in water at room temperature to afford the corresponding N-benzyl-3-alkyl-2-azanorborn-5-ene (III), as described by S. D. Larsen and P. A. Grieco, J. Amer. Chem. Soc., 107, 1768–69 (1985). The aldehyde, benzylamine hydrochloride and cyclopentadiene used in these reactions are commercially available.

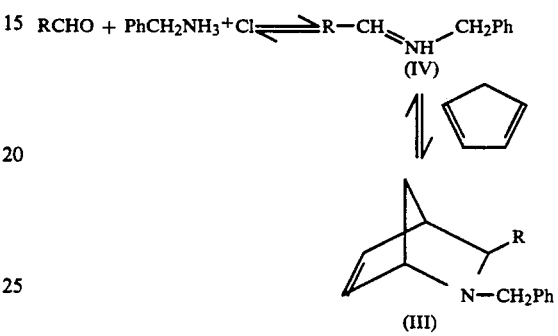

The azanorbornenes (III) are unstable under acid conditions and can revert to the imine (IV) and cyclopentadiene (P. A. Grieco and J. D. Clark, J. Org. Chem., 55, 2271–72 (1990)). The imine (IV) can in turn hydrolyze back to the aldehyde and amine. The reversal is accelerated by the addition of a trap for the cyclopentadiene, e.g., maleimide (P. A. Grieco, D. T. Parker, W. F. Fobare and R. Ruckle, J. Amer. Chem. Soc., 109, 5859–61 (1987) or the imine, i.e., PCl$_3$ (D. A. Cortes, U.S. Pat. No. 4,946,993, Aug. 7, 1990), or Et$_3$SiH (P. A. Grieco and A. Bahsas, J. Org. Chem., 52, 5746–49 (1987). Under basic conditions the azanorbornenes (III) are stable (e.g., several months at 5° C.) and can be isolated by distillation.

The azanorbornene compounds useful in the practice of this invention include for example, N-benzyl-3-methyl-2-azanorborn-5-ene, N-benzyl-3-ethyl-2-azanorborn-5-ene, and N-benzyl-3-isopropyl-2-azanorborn-5-ene. Preferably the azanorbornene is N-benzyl-3-methyl-2-azanorborn-5-ene.

To carry out the method of the present invention, the azanorbornenes may be dissolved in a solvent such as a lower alkyl alcohol. Preferably the lower alkyl alcohol is methanol. The lower alkyl alcohol is present in an amount ranging from about 10 to about 500 moles of the lower alkyl alcohol relative to each mole of the azanorbornene. Most preferably, there are about 100 moles of the lower alkyl alcohol for each mole of azanorbornene.

To the solution of the azanorbornene in the lower alkyl alcohol is added acetic acid, ammonium formate and a transition metal catalyst. The acetic acid may be added in an amount equal to about 0.5 to about 5.0 moles of acetic acid per mole of the azanorbornene. Preferably about 1 to about 2 moles of acetic acid are present for each mole of the azanorbornene. Most preferably, about 1.5 moles of acetic acid are present for each mole of the azanorbornene.

The ammonium formate may be added in an amount equal to about 4 to about 10 moles of ammonium formate per mole of the azanorbornene. Preferably about 5 to about 7 moles of ammonium formate are present for each mole of the azanorbornene. Most preferably, about 6 moles of ammonium formate are present for each mole of the azanorbornene.

Preferably the transition metal catalyst is a palladium on charcoal catalyst (Pd/C). Most preferably the transition metal catalyst is a 10% Pd/C catalyst. This catalyst is available from commercial sources.

The 10% Pd/C catalyst may be present in an amount of about 10 to about 100 grams of the 10% Pd/C catalyst per mole of the azanorbornene. Preferably about 25 to about 50 grams of the 10% Pd/C catalyst are present for each mole of the azanorbornene. Most preferably, about 35 grams of the 10% Pd/C catalyst are present for each mole of the azanorbornene.

The reaction may be carried out by stirring a mixture of the azanorbornene compound in the solvent/reductant/catalyst system under nitrogen at a temperature from about 5° C. up to a temperature of about 50° C. for a reaction time of about 1 to about 20 hours. Preferably, the reaction is carried out at a temperature of about 25° C. for about 18 hours.

After completion of the reaction, the catalyst is removed by any appropriate method such as filtration, the reaction medium is acidified with a mineral acid, the lower alkyl alcohol solvent is removed by distillation, the acid is neutralized with an alkaline metal hydroxide to a pH of about 8 to 12, the free amine is extracted with a suitable water-immiscible organic solvent and the free amine is then recovered from the extract. The mineral acid is preferably selected from the group consisting of hydrochloric, sulfuric and phosphoric acids. Most preferably the mineral acid is hydrochloric acid. The water-immiscible solvent is preferably selected from the group consisting of ether, ethyl acetate, toluene, dichloromethane, chloroform, pentane and hexane. Most preferably, the water-immiscible solvent is pentane. The alkaline metal hydroxide is preferably selected from the group consisting of lithium, sodium, potassium, magnesium and calcium hydroxides. Most preferably, the alkaline metal hydroxide is sodium hydroxide. The mineral acid is most preferably neutralized to a pH of about 12.

The reaction as described relates to the reduction of an azanorbornene using readily available materials, such as a lower alkyl alcohol, acetic acid, ammonium formate and a 10% Pd/C catalyst, that are compatible with the high-yield production of compounds suitable for use in edible food compositions.

The dipeptide amide artificial sweetener of the present invention may be prepared by any of a number of methods where, for example, the appropriate amine is reacted with a suitable dipeptide amide precursor. See, for example, U.S. Pat. No. 4,411,925.

EXAMPLES

Example 1

Catalytic hydrogenation of the azanorbornene N-benzyl-3-methyl-2-azanorborn-5-ene (N-benzyl-2-aza-3-methyl-bicyclo [2.2.1]hept-5-ene) (compound III, with R=CH3)

This example demonstrates that without proper selection of the solvent/reductant/catalyst system the results of this invention are not achieved.

The azanorbornene used in this example, (bp. 74°-80° C., 0.1 mm), was prepared as described by Larsen and Grieco, *J. Am. Chem. Soc.,*, 107, 1768–69 (1985). Five grams of the azanorbornene were dissolved in 100 ml of the appropriate solvent (see Table I) and hydrogenated with H2 at 40 psi for 2 hours at room temperature on a Parr shaker using 400 mg of 10% Pd/C as catalyst. The catalyst was removed by filtration through a Celite ® filter material (available from Celite Corporation, Lompoc, Calif.) and the filtrate evaporated to a thick oil. The residue was dissolved in 100 ml H2O and the pH adjusted to 13 with NaOH. The basic solution was extracted three times with 50 ml diethyl ether, the combined ether extracts were dried over Na2SO4, and then evaporated to leave a thick oil-like product.

The isomer ratios in the product were determined by GLC on a 12 meter (0.32 mm id.) non-polar fused silica column with an SE 30 stationary phase. The temperature was held at 60° C. for 10 minutes and then programmed at 6° C./minute to 195° C. Retention times were 25.0 and 25.2 minutes for the N-benzyl-exo and endo-3-methyl-2- azanorbornanes, and 27.0 mintes for the N-benzyl-1-cyclopentylethyl amine.

The results of the hydrogenations are given in Table I. The product structures were confirmed by GC-Ms analysis.

TABLE I

Relative amounts of products formed during the Pd/C hydrogenation of N-benzyl-2-methyl-azanorbornene (III) at 40 psi in various solvents.

Products*

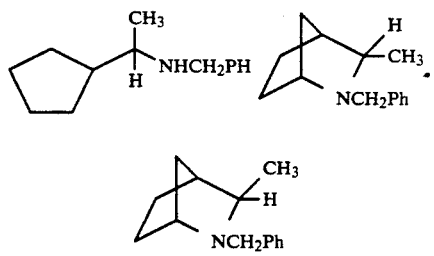

| Solvent | Yields | | |
|---|---|---|---|
| Methanol | 9 | 25 | 66 |
| 1% HOAc-Methanol | 21 | 26 | 53 |
| 10% HOAc-Methanol | 34 | 28 | 38 |
| 100% HOAc | 20 | 30 | 50 |
| Methanol-1 equiv. HCL | 1 | 39 | 60 |
| Methanol-1 equiv. HOAc 2 equiv. NH4OAc | 38 | 19 | 43 |

*It is assumed that the exo product is more abundant, as noted by Larsen and Grieco (J. Amer. Chem. Soc., supra.)

Example 2

Synthesis of 1-cyclopentylethyl amine (compound I, with R=CH3) by transfer hydrogenolysis To a solution of 40 g (0.197 moles) N-benzyl-3-methyl-2-azanorborn-5-ene in 900 ml methanol was added 20 ml (0.35 moles) acetic acid, 80 g (1.27 moles) ammonium formate and 7 g of 10% Pd/C. The mixture was stirred at room temperature under N2 for 4 hours. Considerable initial gas evolution was observed. The catalyst was removed by filtration through a Celite ® filter material and 220 ml 1N hydrochloric acid was added to the filtrate. The solution was then concentrated in vacuo (<30° C.) to approximately 200 ml. The aqueous residue was adjusted to pH 12 with solid NaOH pellets (with cooling) and extracted three times with 100 ml diethyl ether. The combined ether layers were dried over Na2SO4 and then the ether was removed by distillation at atmospheric pressure. The residue was distilled through a short column to give 18.1 g (a yield of 79%) of 1-cyclopentylethyl amine, bp. 149°-55° C. [lit. bp. 149° C., (750 mm), P. A. S. Smith, D. R. Baer and S. N. Ege *J. Amer. Chem. Soc.*, 76. 4564–70 (1954)].

$^{13}$C NMR (CDCl$_3$, 50 MHz) δ:24.4, 27.1, 31.4, 50.8 and 53.8 ppm.

$^1$H NMR (CDCl$_3$, 200 MHz) δ:2.55 (1H, m. CH—N), 0.8–1.8 (9 H, m., CH) and 0.96, 0.99 (d, 3H, CH$_3$).

The amine hydrochloride had mp. 192°–94° C.

$^{13}$C NMR (D$_2$O, 50 MHz) δ:21.32, 29.05, 29.30, 33.06, 33.51, 48.39 and 56.96 ppm.

EXAMPLE 3

Synthesis of 1-cyclopentylmethyl amine (compound I, with R=H) by transfer hydrogenolysis A solution of 40.0 g (0.22 moles) of N-benzyl-2-azanorborn-5-ene (compound III, with R=H) (bp. 93–94° C./0 6 mm) prepared as described by Larsen and Grieco, *J. Amer. Chem. Soc.*, supra), 80 g ammonium formate (1.27 moles) and 20 ml acetic acid (0.35 moles) in 800 ml methanol under N$_2$ was treated with 7.5 g of 10% Pd/C. The mixture was stirred for 18 hours at room temperature and then worked up as in Example 2.

Distillation gave 14.4 g of product (a yield of 67%), bp. 136°–38° C. [lit. b.p., 138°–40° C.; T. J. Cogdell. *J. Org. Chem.*, 37, 2541 (1972)]. By GLC analysis, the product 1-cyclopentylethyl amine had 13% 2-azanorbornane as an impurity.

$^1$H NMR (CDCl$_3$, 200 MHz) δ: 2.49 (d., 2H, —CH$_2$ NH$_2$) and 0.9–1.8 (m., 9H, CH) ppm.

$^{13}$C NMR (CDCL$_3$; 50 MHz) δ: 27.1, 31 9, 45.2 and 49.5 ppm.

Example 4

Synthesis of L-aspartyl-D-alanine-N-(S)-1-cyclopentylethyl amide a) Enrichment of (R,S)-1-cyclopentylethyl amine A mixture of 15.0 g (R,S)-1-cyclopentylethyl amine (0.133 moles), 24.0 g (0.12 moles) D(+)-camphoric acid, 400 ml ethanol and 800 ml acetonitrile were heated until solution was complete. Standing at room temperature overnight afforded 17.4 g of white crystals. These were recrystallized five times from ethanol/CH$_3$CN(¼) as a 2% solution. This afforded 4.01 g of crystals of an (R,S) mixture enriched with the S-enantiomer and having an S/R enantiomer ratio of about 3/1. Further recrystallizations did not improve the S/R ratio.

The 1-cyclopentylethyl amine (S/R=3/1) was converted to the hydrochloride by dissolving the combined product of 3 runs (12.4 g) in 200 ml H$_2$O, adjusting the pH to 12.0 with solid NaOH pellets and extracting three times with 100 ml diethyl ether. The combined ether extracts were dried over Na$_2$SO$_4$, then treated with a solution of 2 g HCl in 100 ml methanol (with cooling) and this solution was evaporated to give 1-cyclopentylethyl amine hydrochloride as a white solid - 8.46 g, mp 192– 4° C.

b) β-benzyl-N-carbobenzyloxy-L-aspartyl-D-alanine-(R,S)-1-cyclopentylethyl amide To a solution of a protected dipeptide of 1.37 g (3.20 mmoles) β-benzyl-N-carbobenzyloxy-L-aspartyl-D-alanine (prepared as described in U.S. Pat. No. 4,411,925), 475 mg (3.22 mmoles) 1-cyclopentylethyl amine hydrochloride (S/R=3/1), 665 mg (3.22 mmoles) dicyclohexyl-carbodiimide and 330 mg (1.84 mmoles) N-hydroxy-5-norbornene-2,3-dicarboximide in 40 ml dioxane was added 450 μl (327 mg, 3.23 mmoles) triethylamine. The solution was stirred at room temperature overnight, then filtered and the filtrate evaporated to give an amorphous solid. The solid was dissolved in 300 ml ethyl acetate and extracted two times with 75 ml of 4% aqueous citric acid, three times with 100 ml 4% aqueous NaHCO$_3$ and 50 ml brine. Drying (with Na$_2$SO$_4$) and evaporation of the ethyl acetate gave a white solid, which was recrystallized from ethyl acetate/hexane to give 1.60 g (2 crops) of white solid (3.05 mmoles, 95%) mp. 189°–91° C.

$^1$H NMR (CDCl$_3$, 200 MHz) δ 7.30 (10 H, ArH, m), 6.90 (1H, NH, d), 6.30 (1H, NH, d), 5.12 (4H, 2CH$_2$O, m), 4.61 (1H, CO/CHN, m), 4.39 (1H, CO/CHN, m), 3.80 (1H, —N—CH-C(CH3), m), 3.07 (1H, CH$_2$CO$_2$H,q), 2.82 (1H, CH$_2$CO2H,q), 1.05–1.75 (9H, —CH$_2$ and —CH—, m), 1.31 (3H, —CH$_3$ d) and 1.15 (3H, CH$_3$, d)

$^{13}$C NMR (CDCl$_3$, 50 MHz) 173.8, 172.8, 172.3, 137.8, 137.2, 130.7, 130.5, 130.3, 69.4, 68.9, 53.2, 51.5, 51.4, 47.9, 38.0, 31.5, 31.3, 27.4, 27.1, 21.6 and 19.6 ppm.

c) L-aspartyl-D-alanine-(S)-1-cyclopentylethyl amide 500 mg 10% Pd/C was added to a solution of 4.5 g (8.60 mmoles) N-carbobenzyloxy-β-benzyl-L-aspartyl-D-alanine-1-cyclopentylethyl amide (from Part b) in 250 ml methanol. The mixture was hydrogenated at 40 psi for 4 hours, then the catalyst removed by filtration through a Celite ® filter material. The Celite ® filter material was then washed twice with 50 ml H$_2$O and the combined methanol water filtrate concentrated to 100 ml in vacuo. This solution was diluted with 100 ml H$_2$O, warmed to 50° C., and then filtered. The aqueous filtrate was freeze-dried to afford 2.55 g (8.5 mmoles) of L-aspartyl-D-alanine-1-cyclopentylamide. HPLC analysis using a C-18 column and 20% CH$_3$CN in 80% 0.2% KH$_2$PO$_4$ buffer pH 4.0 as eluant showed two peaks with a ratio of 6:1, representing the S and R isomers of the cyclopentylethyl amides. Three recrystallizations of the product from 95% ethanol gave 610 mg of the pure L-aspartyl-D-alanine-(S)-1-cyclopentylethyl amide, mp 204°–5° C.

$^1$H NMR (D$_2$O, 200 MHz) δ4.20 (m, 2H, —CO—CH—N), 3.62 (m, 1H, HN—CH—CH$_3$), 2.73 (m, 2H, —CH$_2$CO$_2$H), 1.0–1.8 (m, 9H, —CH— and —CH$_2$—), 1.35 (dd, 3H, CH$_3$) and 1.09 (dd, 3H, CH$_3$)

$^{13}$C NMR (D$_2$O, 50 MHz) δ 180.6, 178.2, 173.8, 54.98, 54.61, 54.44, 49.56, 41.33, 33.59, 33.35, 29.33, 29.04, 22.96 and 21.05

When tasted in H$_2$O at 125 ppm, the sample was isosweet to 250 ppm aspartame. This corresponds to a sweetness potency of 400× sucrose.

The sweetener compounds and the physiologically acceptable salts thereof of the present invention provide advantages as sweetening agents in view of their high sweetness potency, their physical form and stability. They are, ordinarily, crystalline, non-hygroscopic, water-soluble solids. They are characterized by possessing a sweet taste and are devoid of undesirable harsh or bitter flavor qualities at ordinary use levels.

The compounds of the invention can be prepared in a variety of forms suitable for utilization as sweetening agents. Typical forms that can be employed are solids, such as powders, tablets, granules and dragees, and liquid forms, such as solutions, suspensions, syrups, emulsions, as well as other commonly employed forms that are particularly suited for combination with edible materials. These forms can comprise compounds of the present invention, or of their physiologically acceptable salts, either apart or in association with non-toxic sweetening agent carriers, e.g.. non-toxic substances commonly employed in association with sweetening agents. Such suitable carriers include liquids such as water, ethanol, sorbitol, glycerol, corn oil, peanut oil, soybean oil, sesame oil, propylene glycol, corn syrup, maple syrup and liquid paraffin, and solids such as citric acid, lactose, cellulose, starch, dextrin, modified starches, polysaccharides such as polydextrose (see, e.g. U.S. Pat. Nos. 3,766,165 and 3,876,794), calcium phosphate (mono-, di- or tri-basic) and calcium sulfate.

The sweeteners of this invention may be used to provide desirable properties of sweetness in any orally ingestible product. Examples of specifically ingestible materials include: fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, beverages such as coffee, tea, carbonated and non-carbonated soft drinks, beers, wines and liquors; confections such as candy and fruit flavored drops, condiments such as herbs, spices and seasonings, flavor enhancers such as monosodium glutamate and chewing gum. The instant sweeteners may also be useful in prepared packaged products such as dietetic sweeteners, liquid sweeteners, granulated flavor mixes, which upon reconstitution with water provide non-carbonated drinks, instant pudding mixes, instant coffee and tea, coffee whiteners, malted milk mixes, pet foods, livestock feed, tobacco and personal care products such as mouth washes and toothpaste, as well as proprietary and non-proprietary pharmaceutical preparations and other products of the food, pharmaceutical and sundry industries. Especially preferred sweetened edible compositions are carbonated beverages containing one or more of the subject sweeteners. The sweeteners could also be used in frozen desserts, baked goods, chewing gum, dentifrices, medications or any other orally ingestible substance.

The sweeteners of this invention may also be blended with other sweeteners known to the art, such as, for example, sucrose, fructose, saccharin, Acesulfame-K, cyclamate, Aspartame, sucralose and the like, which are useful for sweetening edible materials. Especially useful are the blends of the sweeteners of this invention and saccharin or physiologically acceptable salts thereof. Examples of saccharin salts include the sodium, potassium, calcium and ammonium salts. Examples of the sweeteners of this invention also include their sulfates, malates, hydrochlorides, carbonates, phosphates, citrates, benzoates and the like. In blends with saccharin the compounds of this invention may reduce or completely mask the well known, undesirable bitter aftertaste of the saccharin.

What is claimed is:

1. A process for making a 1-cyclopentylalkyl amine comprising the steps of reducing an N-benzyl-3-alkyl-2-azanorborn-5-ene in a lower alkyl alcohol solvent in the presence of acetic acid, ammonium formate and a transition metal catalyst to produce a 1-cyclopentylalkyl amine having the structure:

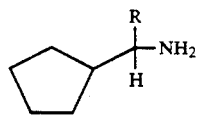

wherein R is an alkyl group.

2. The process according to claim 1 wherein said transition metal catalyst comprises 10% palladium on charcoal.

3. The process according to claim 2 wherein R is selected from the group consisting of straight chain alkyl groups of 1 to 4 carbons, branched alkyl groups of 3 to 6 carbons and cycloalkyl groups of 3 to 6 carbons.

4. The process according to claim 3 wherein R is a methyl group.

5. The process according to claim 1 wherein said lower alkyl alcohol is methanol.

6. The process according to claim 1 wherein said reduction is carried out under an inert atmosphere at a temperature from about 5° C. to about 50° C. for a reaction time of about 1 to about 20 hours.

7. The process according to claim 6 wherein the temperature is about 20° C. to about 30° C. and the reaction time is about 18 hours.

8. The process according to claim 7 wherein the temperature is about 25° C.

9. A process for making an artificial dipeptide amide sweetener comprising the steps of:
    preparing an (R,S) mixture of 1-cyclopentylalkyl amine by reducing an azanorbornene in a lower alkyl alcohol solvent in the presence of acetic acid, ammonium formate and a transition metal catalyst;
    enriching the (R,S) mixture to produce a mixture enriched with the S-enantiomer;
    coupling a protected L-aspartyl-D-α-amino alkanoic acid with the 1-cyclopentylalkyl amine of said enriched mixture to produce a protected L-aspartyl-D-α-amino alkanoic acid-1-cyclopentylalkyl amide; and
    deprotecting the protected-L-aspartyl D-α-amino alkanoic acid -1-cyclopentylalkyl amide to produce an artificial dipeptide amide sweetener.

10. The process according to claim 9 wherein the protected L-aspartyl D-o-amino alkanoic acid comprises B-benzyl-N-carbobenzyloxy-L-aspartyl-D-alanine.

11. The process according to claim 9 wherein the 1-cyclopentylalkyl amine comprises 1-cyclopentylethyl amine.

12. The process according to claim 9 wherein the protected L-aspartyl-D-α-amino alkanoic acid amide is deprotected by a hydrogenation step.

13. The process according to claim 12 wherein said hydrogenation step comprises hydrogenating with 10% palladium on charcoal as catalyst.

14. The process according to claim 9 wherein the enriched mixture has an S/R enantiomer ratio of about 3/1.

15. A process for making a 1-cyclopentylalkyl amine comprising:
    dissolving a N-benzyl-3-alkyl-2-azanorborn-5-ene compound in a lower alkyl alcohol solvent;
    adding a reducing composition of acetic acid, ammonium formate and a transition metal catalyst;

reducing said N-benzyl-3-alkyl-2-azanorborn-5-ene with said reducing composition under an inert atmosphere;

acidifying with an aqueous acid;

removing the lower alkyl alcohol solvent by distillation;

neutralizing the acid with an aqueous alkaline metal hydroxide up to a pH of about 8 to about 12;

extracting the 1-cyclopentylalkyl amine with a suitable water-immersible organic solvent; and recovering said amine from the extract.

16. The process according to claim 15 wherein the inert atmosphere comprises nitrogen.

17. The process according to claim 15 wherein the 1-cyclopentylalkyl amine comprises 1-cyclopentylethyl amine.

18. The process according to claim 15 wherein the transition metal catalyst comprises 10% palladium on charcoal.

19. The process according to claim 15 wherein the lower alkyl alcohol is methanol.

20. The process according to claim 15 wherein the temperature of the reaction is about 20° C. to about 30° C. and the reaction time is about 4 to about 20 hours.

21. The process according to claim 20 wherein the reaction time is about 18 hours.

22. The process according to claim 20 wherein the temperature of the reaction is about 25° C.

23. The process according to claim 15 wherein the acidifying acid is a mineral acid.

24. The process according to claim 23 wherein the mineral acid is selected from the group consisting of hydrochloric, sulfuric and phosphoric acid.

25. The process according to claim 24 wherein the mineral acid is hydrochloric acid.

26. The process according to claim 15 wherein the water-immiscible solvent is selected from the group consisting of ether, ethyl acetate, toluene, dichloromethane, chloroform, pentane and hexane.

27. The process according to claim 26 wherein the water-immiscible solvent is pentane.

28. The process according to claim 15 wherein the alkaline metal hydroxide is selected from the group consisting of lithium, sodium, potassium, magnesium and calcium hydroxide.

29. The process according to claim 28 wherein the alkaline metal hydroxide is sodium hydroxide.

* * * * *

UNITED STATES PATENT AND TRADEMARK OFFICE
CERTIFICATE OF CORRECTION

PATENT NO. : 5,225,591
DATED : July 6, 1993
INVENTOR(S) : Sweeny et al.

It is certified that error appears in the above-identified patent and that said Letters Patent is hereby corrected as shown below:

Title page item [54] line 2, and

Column 2, line 1 change "1-CYCLOPENTYLALYL" to
--1-CYCLOPENTYLAKYL--;

Column 1, line 2, change "1-CYCLOPENTYLALYL" to
--1-CYCLOPENTYLAKYL--;

Column 6, line 21, change "GC-Ms" to --GC-MS--;

UNITED STATES PATENT AND TRADEMARK OFFICE
CERTIFICATE OF CORRECTION

PATENT NO. : 5,225,591
DATED : July 6, 1993
INVENTOR(S) : Sweeny et al.

It is certified that error appears in the above-identified patent and that said Letters Patent is hereby corrected as shown below:

Column 6, lines 23-48, change TABLE I to:

Table I. Relative amounts of products formed during the Pd/C hydrogenation of N-benzyl-2-methyl-azanorbornene (III) at 40 psi in various solvents.

Products*

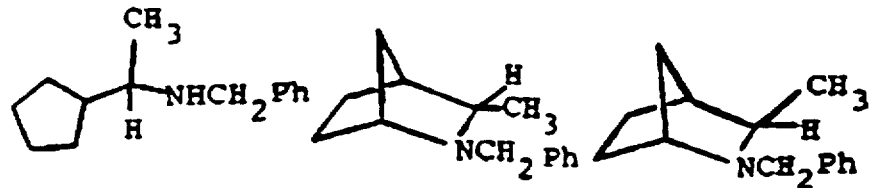

| Solvent | Yields | | |
|---|---|---|---|
| Methanol | 9 | 25 | 66 |
| 1% HOAc-Methanol | 21 | 26 | 53 |
| 10% HOAc-Methanol | 34 | 28 | 38 |
| 100% HOAc | 20 | 30 | 50 |
| Methanol-1 equiv. HCL | 1 | 39 | 60 |
| Methanol-1 equiv. HOAc 2 equiv. $NH_4OAc$ | 38 | 19 | 43 |

\* It is assumed that the exo product is more abundant, as noted by Larsen and Grieco (*J. Amer. Chem. Soc.*, supra.)

UNITED STATES PATENT AND TRADEMARK OFFICE
CERTIFICATE OF CORRECTION

PATENT NO. : 5,225,591
DATED : July 6, 1993
INVENTOR(S) : Sweeny et al.

It is certified that error appears in the above-identified patent and that said Letters Patent is hereby corrected as shown below:

Column 7, line 19 change "C./06" to --C./0.6--;

Column 8, line 16, change at both occurrences "CO/CHN,"

to --CO/C̲HN--;

Column 8, line 46, change "δ4.20" to --δ 4.20--;

Column 8, line 47, change "-CH-" to -- -C̲H- --;

Column 8, line 48, change "-CH2 CO$_2$H" to

-- -CH$_2$CO$_2$H --.

Column 10, line 47, change "D-o-amino" to

--D-α-amino--.

Signed and Sealed this

Seventeenth Day of May, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,225,591
DATED : JULY 6, 1993
INVENTOR(S) : SWEENY ET AL.

It is certified that error appears in the above-indentified patent and that said Letters Patent is hereby corrected as shown below:

Title page, item [54] line 2 (title), and

Column 1, line 2, change "1-CYCLOPENTYLALYL" TO

--1-CYCLOPENTYLALKYL--.

Signed and Sealed this

Thirtieth Day of May, 1995

Attest:

BRUCE LEHMAN

*Attesting Officer*     *Commissioner of Patents and Trademarks*